United States Patent [19]

Cannata et al.

[11] Patent Number: 5,550,287

[45] Date of Patent: Aug. 27, 1996

[54] PROCESS FOR THE PREPARATION AND PURIFICATION OF IODINATED CONTRAST AGENTS

[75] Inventors: Vincenzo Cannata, Sasso Marconi; Valeriano Merli, Occhiobello; Claudio Dal Santo, Monticello Di Fara, all of Italy

[73] Assignee: Zambon Group S.p.A., Vicenza, Italy

[21] Appl. No.: 397,955

[22] Filed: Mar. 3, 1995

[30] Foreign Application Priority Data

Mar. 3, 1994 [IT] Italy ................................ MI94A0378

[51] Int. Cl.⁶ ........................ C07C 233/05; C07C 231/22
[52] U.S. Cl. .................. 564/153; 424/9.452; 424/9.451; 424/9.45
[58] Field of Search ............... 424/9.452, 9.451, 424/9.45; 564/153

[56] References Cited

U.S. PATENT DOCUMENTS

| | | | |
|---|---|---|---|
| 4,348,377 | 9/1982 | Felder et al. | 424/5 |
| 5,019,371 | 5/1991 | Lin et al. | 424/5 |
| 5,066,823 | 11/1991 | Felder et al. | 560/13 |

FOREIGN PATENT DOCUMENTS

| | | |
|---|---|---|
| 1472050 | 4/1977 | European Pat. Off. . |
| 0026281 | 4/1981 | European Pat. Off. . |
| 0575717A1 | 12/1993 | European Pat. Off. . |
| 1472050 | 4/1977 | United Kingdom . |

OTHER PUBLICATIONS

Analytical Profiles of Drug Substances vol. 17 edited by Klaus Florey; Cover Sheet & p. 138.

Ion Exchange in the Processing of Non–Ionic X–Ray Contrast Media; Cover sheet & PP V–37 –V–43 Nyegaard & Co A/S, Oslo 4, Norway.

J.C.S. Chem. Comm. 1981; pp. 760 and 761.

Derwent Abstract No. 65409y coressponding to Japanese patent application No. 49/56989 Kyowa Hakko Kogyo Co. Ltd.

Oslo Symposium 1982, pp. V–36–V–43, 1982, T. Gulbrandsen, "Ion Exchange in the Processing of Non–Ionic X–Ray Contrast Media".

*Primary Examiner*—Shailendra Kumar
*Attorney, Agent, or Firm*—Oblon, Spivak, McClelland, Maier, & Neustadt, P.C.

[57] ABSTRACT

A process for the preparation and purification of L-5-(2-hydroxypropionylamino)-2,4,6-triiodoisophthalic acid bis-(1,3-dihydroxypropylamide) by using ion-exchange resins is described.

8 Claims, No Drawings

PROCESS FOR THE PREPARATION AND PURIFICATION OF IODINATED CONTRAST AGENTS

The present invention relates to a process for the preparation and purification of iodinated contrast agents and more particularly it relates to a process for the preparation and purification of L-5-(2-hydroxypropylamino)- 2,4,6-triiodoisophthalic acid bis-(1,3-dihydroxypropylamide) by using ion-exchange resins.

The compound L-5-(2-hydpoxypropionylamino)-2,4,6-triiodoisophthalic acid bis-(1,3-dihydpoxypropylamide), which will be indicated hereinafter with its International non-proprietary name Iopamidol, has been described for the first time in the British patent no. 1472050 (Savac AG).

Iopamidol is used in diagnostics as X-ray non-ionic contrast agent. For its use in diagnostics, Iopamidol and generally all the iodinated contrast agents are administered at high doses and therefore they must have extremely high requirements of purity.

The synthesis of Iopamidol described in the British patent no. 1472050, which is the industrial synthesis of the compound as far as we know, consists in the following steps:
1. preparation of 5-amino-2,4,6-triiodoisophthalic acid by iodination of 5-aminoisophthalic acid;
2. preparation of 5-amino-2,4,6-triiodoisophthalic acid dichloride;
3. reaction of 5-amino-2,4,6-triiodoisophthalic acid dichloride with L-2-acetoxypropionic acid chloride to give L-5-(2-acetoxypropionylamino)- 2,4,6-triiodoisophthalic acid dichloride (compound A);
4. reaction of compound A with 2-amino-1,3-propanediol in an aprotic solvent, usually dimethylacetamide, and in the presence of a base to obtain L-5-(2-acetoxypropionylamino)-2,4,6-triiodoisophthalic acid bis-(1,3-dihydroxypropylamide) (compound B);
5. basic hydrolysis of compound B to obtain crude Iopamidol;
6. purification of the crude Iopamidol by de-salting through resins and subsequent repeated crystallizations.

The purification step of the crude Iopamidol (step 6) is particularly long and difficult because, as already underlined, the purity requirements of Iopamidol must be extremely high and, in the meantime, the impurities in the etude product are difficult to be separated.

The resins used in the purification step are usually weak anionic resins.

In fact, the use of anionic resins for the purifications of compounds is well-known. In some cases, it has also been described in literature that compounds such as glycerophospholipids (European patent application No. 0575717—Chemi S.p.A.), megalomycin A O-acyl derivatives (Derwent Abstract No. 65409y corresponding to Japanese patent application No. 49/56989—Kyowa Hakko Kogyo Co. Ltd.) and acylated sugars [J. Chem. Soc., Chem. Commun. (15), 760-1, (1981)] can be deacylated with basic ion-exchange resins.

However, the use of strong anionic resins for the preparation and/or purification of Iopamidol has never been described in literature, as far as we know.

Furthermore, Trygve Gulbrandsen (Oslo Symp. 1982: Ion Exch. Solvent Extr., Pap. 1982, V/36–V/43) describes the disadvantages met in the purification of two different iodinated contrast agents, Metrizamide and Iohexol, by using strong anionic resins. In particular, the Author describes that the use of strong anionic resin Amberlite IRA-900 yielded the formation of by-products so reaching to the conclusion that such a resin had to be substituted in the process for purification of Iohexol.

We have now found that the preparation and purification of Iopamidol can be advantageously carried out starting from the intermediate L-5-(2-acetoxypropionylamino)-2,4,6-triiodoisophthalic acid bis-( 1,3-dihydroxypropylamide) (compound B) by using first a strong anionic resin and then a weak anionic resin.

Therefore, object of the present invention is a process for the preparation and purification of L-5-(2-hydroxypropionylamino)-2,4,6-triiodoisophthalic acid bis-(1,3-dihydroxypropylamide) comprising the loading of a solution of crude L-5-(2-acetoxypropionylamino)- 2,4,6-triiodoisophthalic acid bis-(1,3-dihydroxypropylamide) on a column containing a strong anionic resin, the elution with water, the elution with a diluted aqueous solution of a weak acid so that crude L-5-(2-hydroxypropionylamino)-2,4,6-triiodoisophthalic acid bis-(1,3-dihydroxypropylamide) is released out of the column and the final purification of the resultant etude by chromatography on a weak anionic resin.

Iopamidol obtained by the process object of the present invention is characterized by a high purity and it is particularly suitable for diagnostic use.

Preferably, the solution of crude L-5-(2-acetoxypropionylamino)- 2,4,6-triiodoisophthalic acid bis-(1,3-dihydroxypropylamide) (Compound B) is a solution in a mixture of water and an aprotic polar solvent.

From a practical point of view, the aprotic solvent usually present in the solution is dimethylacetamide, that is the solvent used in the reaction for the preparation of compound B.

Still more preferably, the solution is a mixture deriving from the reaction between L-5-(2-acetoxypropionylamino)-2,4,6-triiodoisophthalic acid dichloride and 2-amino-1,3-propanediol, suitably de-salted.

The strong anionic resin is preferably a resin consisting of quaternary ammonium groups bound to a polymeric supporting material. Specific examples of strong anionic resins which can be used in the process object of the present invention are resins with a styrene-divinylbenzene matrix such as those commercialized with the trade name "Amberlite IRA 900" or "IMAC HP 551".

These strong anionic resins are able to fix and hydrolise Compound B and allow to remove from the reaction mixture all the possibly present impurities having an acidity substantially lower than that of Compound B or of Iopamidol. In practice, compounds having an acidity up to 10 times lower than that of Iopamidol are fixed on the resin (Iopamidol $pK_a$=10.7, Analytical Profiles of Drug Substances, vol. 17, page 138 edited by Klaus Florey, Academic Press Inc., 1988). The main impurity having this characteristic is the reaction solvent, usually dimethylacetamide.

In this connection, it is worth underlining that dimethylacetamide is a very difficult solvent to be removed because it is highly soluble in water and has a high boiling point (about 165° C.).

Of course, the presence of, even if very little, amounts of dimethylacetamide or, in any case, of organic solvents is absolutely unacceptable in relation with the characteristics of pharmacological safety required for a compound to be administered in so high doses such as those needed for X-ray diagnosis.

The diluted aqueous solution of a weak acid to be used in the process object of the present invention is preferably a diluted aqueous solution of acetic acid.

This acid solution is useful for releasing Iopamidol from the strong anionic resin. Then, crude Iopamidol is eluted out of the column. The hydrolysis of compound B, carried out according to the process of the present invention, is characterized by the absence of racemization by-products.

Furthermore, the crude Iopamidol obtained after elution out of the column containing the strong anionic resin has already a high purity degree since it is free from impurities, such as for example dimethylacetamide, which are, on the contrary, usually present at this stage of the synthesis in the known industrial processes.

It is also worth underlining that the purity of the crude Iopamidol obtained by the process object of the present invention allows to make easier and efficient the subsequent final purification of the product.

The final purification of Iopamidol according to the process of the present invention is preferably carried out by chromatography, by using a column containing a weak anionic resin.

The weak anionic resin is preferably a resin consisting of dialkylamino groups bound to a polymeric supporting material.

Specific examples of weak anionic resins which can be used in the process object of the present invention are resins with a styrene-divinylbenzene matrix such as those commercialized with the tradename "Amberlite IRA 94 S", "IMAC HP 661" or "Amberlite IRA 93 S".

The crossing of crude Iopamidol, preferably as an eluate directly coming from the previous strong anionic resin column, through this column containing a weak anionic resin allows to purify Iopamidol from all the possibly still present impurities by chromatography. In particular, this chromatographic purification according to the process of the present invention is extremely efficient for the purification of Iopamidol from reaction by-products having very similar solubility characteristics with respect to Iopamidol itself and then very difficultly separable by crystallization.

Iopamidol obtained by the process object of the present invention does not require further purifications since it already has the purity characteristics required by the Health Authorities.

From a practical point of view, it could be optionally crystallized exclusively with the aim of improving the physical characteristics of the product so making it more suitable for formulation.

A practical embodiment of the process object of the present invention is the following.

A solution of L-5-(2-acetoxypropionylamino)-2,4,6-triiodoisophthalic acid bis-(1,3-dihydroxypropylamide) obtained after dilution with water of the mixture of the reaction between L-5-(2-acetoxypropionylamino)- 2,4,6-triiodoisophthalic acid dichloride and 2-amino-1,3-propanediol in dimethylacetamide and in the presence of a base is de-salted (to remove the optional excess of base present in the form of hydrochloride) and then loaded on a strong anionic resin column by eluting with water up to dimethylacetamide stops to let out.

At the end of the elution with water, the column is let rest for some hours in order to complete the hydrolysis and then eluted with a diluted aqueous solution of acetic acid and afterwards with water. The resultant solution, containing crude Iopamidol and the excess of acetic acid, is directly passed across a weak anionic resin column and pure Iopamidol is obtained by chromatographic separation as the product having the highest Rf.

From the resultant aqueous solution of pure Iopamidol, the crystalline product is then isolated according to conventional methods.

As already underlined, the characterizing and innovative feature of the process of preparation and purification of Iopamidol object of the present invention is represented by the use of a strong anionic resin.

In fact, the use of such a resin allows to efficiently purify L-5-( 2-acetoxypropionylamino)-2,4,6-triiodoisophthalic acid bis-(1,3-dihydroxypropylamide) and contemporaneously to hydrolyse it to Iopamidol with practically quantitative yields.

The resultant hydrolysed product (Iopamidol) is not only already purified from optional salts and from traces of impurities, in particular from traces of solvent, but it is practically free from the impurities characterizing the known processes for the hydrolysis of the acetoxy derivative of Iopamidol.

The presence of these impurities, in addition to make Iopamidol absolutely not suitable for diagnostic use, makes particularly laborious and difficult, as a consequence, the final purification of the product.

The use of a strong anionic resin according to the process object of the present invention allows also to purify the final product by chromatography so avoiding to carry out repeated crystallizations from organic solvents.

It is worth underlining that the high purity of the product obtained by the process object of the present invention is still more surprising in view of the fact that in literature it is described how the use of strong anionic resins in the purification of iodinated contrast agents analogs to Iopamidol leads to the formation of remarkable amounts of by-products.

The process of preparation and purification of Iopamidol according to the present invention shows several advantages with respect to the known processes.

The process is made simpler because the purification and hydrolysis are, in practice, carried out in a single step.

The yields of the hydpolysis reaction are practically quantitative and the reaction itself does not give rise to by-products or to racemizations.

The overall yield of the process is very high and, above all, the purity characteristics of the resultant product completely fulfill the specific requirements of the Health Authorities.

With the aim of better illustrating the present invention the following examples are now given.

EXAMPLE 1

In a flask containing dimethylacetamide (1815 g), under stirring, 2-amino-1,3-propanediol (288 g; 2.94 moles) was added.

After cooling at about 15° C., L-5-(2-acetoxypropionylamino)-2,4,6-triiodoisophthalic acid dichloride (500 g; 0.7 moles) was added. The temperature spontaneously rose to about 40° C. within few minutes and was kept at this value fop about 4 hours.

Water (2550 ml) was added to the reaction mixture and the resultant solution was passed across three series columns, filled with IR 120 (1000 ml), IRA 94 S (1750 ml) and IRA 900 (3300 ml) respectively. When the solution finished, the columns were eluted with water collecting about 4.5 liters of water and about 1.5 liters of a solution containing dimethylacetamide and other impurities at the outlet of the column filled with IRA 900.

At this point, the outlet of the column filled with IRA 900 was connected with the inlet of the column filled with IRA 94 S (750 ml).

A 5% aqueous solution of acetic acid (3825 ml) was passed across these two series columns.

At the end of the elution with acetic acid, the columns were eluted with water by collecting the eluate fraction (about 5 l) containing Iopamidol from the outlet of the column filled with IRA 94 S. Charcoal (15 g) was added to this solution and the mixture was kept under stirring for about 5 minutes, filtered on celite and then concentrated up to obtain a solution at about 80%.

This concentrated solution was heated at 85° C. and, in about two hours, 2-butanol (2.75 l) was added by keeping the mixture under reflux.

At the half of the addition, a seed (2 g) of Iopamidol was added. At the end of the addition, the mixture was kept for 30 minutes under reflux, then cooled at room temperature and filtered.

The resultant solid was washed with 2-butanol (2×100 ml) and dried under vacuum at about 50° C. up to constant weight.

450 g (82.7% yield) of pure Iopamidol were obtained.

EXAMPLE 2

In a two liters reactor, with mechanical stirrer and kept under nitrogen, dimethylacetamide (916 g) and 2-amino-1,3-propanediol (278 g) were loaded.

The suspension was cooled at 5° C. and, portionwise, L-5-(2-acetoxypropionylamino)- 2,4,6-triiodoisophthalic acid dichloride (500 g) was added by keeping the temperature between 15° C. and 20° C.

At the end of the addition, the reaction mixture was kept under stirring at 20°–22° C. for about 15 hours.

After dilution with water (1700 g), the resultant solution was clarified through a filter and then passed across the following series columns, filled with IR 120 (1000 ml), IRA 94 S (1750 ml) and IRA 900 (3250 ml) respectively.

When the solution finished, the columns were eluted with water up to dimethylacetamide stopped to come out of the column filled with IRA 900.

At this point, the outlet of the column filled with IRA 900 was connected with the inlet of the column filled with IRA 94 S (1500 ml).

A 5% aqueous solution of acetic acid (3500 ml) was passed across these two series columns.

At the end of the elution with acetic acid, the columns were eluted with water by collecting the eluate fraction containing Iopamidol from the outlet of the column filled with IRA 94 S.

Charcoal (15 g) was added to this solution and the mixture was filtered and concentrated under vacuum up to a concentration of about 75% w/w.

This concentrated solution was heated at 85° C. and, by keeping the mixture at this temperature, 2-butanol (1600 g) was added. The resultant suspension was cooled and filtered.

The resultant solid was washed with 2-butanol and dried under vacuum up to constant weight.

470 g (86% yield) of pure Iopamidol were obtained.

What we claim is:

1. A process for the preparation and purification of L-5-(2-hydroxypropionylamino)- 2,4,6-triiodoisophthalic acid bis-(1,3-dihydroxypropylamide) comprising the loading of a solution of crude L-5-(2-acetoxypropionylamino)- 2,4,6-triiodoisophthalic acid bis-(1,3-dihydroxypropylamide) on a column containing a strong anionic resin, the elution with water, the elution with a diluted aqueous solution of a weak acid so that crude L-5-(2-hydroxypropionylamino)-2,4,6-triiodoisophthalic acid bis-(1,3-dihydroxypropylamide) is released out of the column and the final purification of the resultant crude by chromatography on a weak anionic resin.

2. A process according to claim 1 wherein the solution of crude L-5-(2-acetoxypropionylamino)-2,4,6-triiodoisophthalic acid bis-( 1,3-dihydroxypropylamide) is a solution in a mixture of water and an aprotic polar solvent.

3. A process according to claim 2 wherein the aprotic polar solvent is dimethylacetamide.

4. A process according to claim 1 wherein the strong anionic resin is a resin consisting of quaternary ammonium groups bound to a polymeric supporting material.

5. A process according to claim 1 wherein the strong anionic resin is a resin with styrene-divinylbenzene matrix.

6. A process according to claim 1 wherein the diluted aqueous solution of a weak acid is a diluted aqueous solution of acetic acid.

7. A process according to claim 1 wherein the weak anionic resin is a resin consisting of dialkylamino groups bound to a polymeric supporting material.

8. A process according to claim 1 wherein the weak anionic resin is a resin with a styrene-divinylbenzene matrix.

\* \* \* \* \*